United States Patent
Wu et al.

(10) Patent No.: US 6,245,256 B1
(45) Date of Patent: Jun. 12, 2001

(54) CHIRAL SWALLOW-TAILED LIQUID CRYSTALS AND ITS FABRICATION METHOD

(75) Inventors: Shune-Long Wu; Jang-Jeng Liang, both of Taipei (TW)

(73) Assignee: Chunghwa Picture Tubes, Inc., Taipei (TW)

( * ) Notice: Subject to any disclaimer, the term of this patent is extended or adjusted under 35 U.S.C. 154(b) by 0 days.

(21) Appl. No.: 09/411,866

(22) Filed: Oct. 4, 1999

(30) Foreign Application Priority Data

Jan. 20, 1999 (TW) ................................................ 88100855

(51) Int. Cl.$^7$ .......................... C09K 19/32; C09K 19/34; C09K 19/20; C09K 69/76; C09K 69/753
(52) U.S. Cl. .................. 252/299.6; 252/299.61; 252/299.62; 252/299.66; 252/299.67; 560/100; 544/298; 544/335
(58) Field of Search .......................... 252/299.62, 299.66, 252/299.67, 299.61; 560/56, 100; 544/298, 335

(56) References Cited

U.S. PATENT DOCUMENTS 5,976,409 * 11/1999 Mineta et al. .................. 252/299.65
6,001,278 * 12/1999 Matsumoto et al. ............ 252/299.65

OTHER PUBLICATIONS

Caplus 1996: 36494 1996.*
Caplus 1993: 30426 1993.*

* cited by examiner

Primary Examiner—Shean C. Wu
(74) Attorney, Agent, or Firm—Bacon & Thomas

(57) ABSTRACT

Novel chiral swallow-tailed liquid crystals synthesized from chiral material comprised of alkyl(s)-2-{6-[4-(4'-alkyloxyphenyl)benzoyloxy]-2-naphthyl}propionates having a rigid core, a chiral center directly linked to the rigid core, a chiral tail, and a swallow-tailed group linked to the chiral tail. The chiral center and the swallow-tailed group are arranged at the same side in the molecular structure of the chiral material. These structural characteristics enable the chiral material to have same property of threadholdless antiferroelectricity, and the advantage of simple manufacturing process. The chiral material shows an optimum application effect in liquid crystal displays.

14 Claims, 12 Drawing Sheets

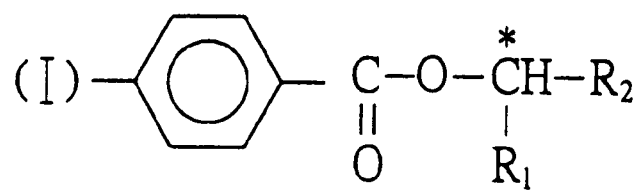
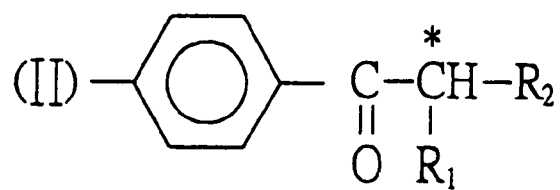
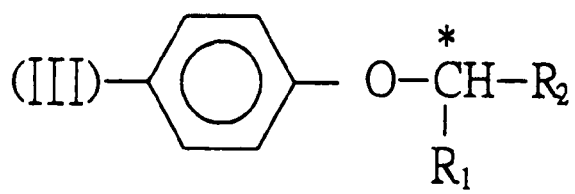
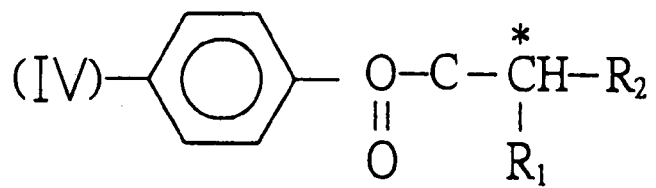
FIG. 8 (Prior Art)

| molecular structure of liquid crystal | phase transferring temperature |
|---|---|
| $C_8H_{17}O-\bigcirc-COO-\bigcirc-COOCH(CH_3)C_6H_{13}$ | Iso 149.6°C $S_A$ 121.5°C $S_C^*$ 117°C $S_{CA}^*$ 72.5°C Cryst. |
| $C_8H_{17}O-\bigcirc-COO-\bigcirc\overset{F}{-}COOCH(CF_3)C_6H_{13}$ | Iso 112.0°C $S_A$ 110.0°C $S_{CA}^*$ −2°C Cryst. |
| $C_9H_{19}-\bigcirc\!\!\!\bigcirc-COO-\bigcirc-COOCH(CF_3)C_6H_{13}$ | Iso 79.9°C $S_A$ 71.5°C $S_C^*$ 70.4°C $S_{CA}^*$ 18.0°C Cryst. |
| $C_{10}H_{21}O-\bigcirc-COO-\bigcirc-COOCH(CH_3)C_4H_9$ | Iso 134.0°C $S_A$ 106.0°C $S_C^*$ 86.0°C $S_C^*$ 73.0°C $S_{CA}^*$ 48.0°C Cryst. |
| $C_9H_{19}COO-\bigcirc-COO-\bigcirc-COOCH(CF_3)C_6H_{13}$ | Iso $S_A$ −4.8°C $S_C^*$ −5.0°C $S_{CA}^*$ −13.0°C $S_X^*$ −42.0°C Cryst. |
| $C_{10}H_{21}O-\bigcirc-COO\!-\!(\bigcirc-COO)_2\!CH(CF_3)C_6H_{13}$ | Iso 180.0°C $S_A$ 140.0°C $S_{CA}^*$ 100.0°C Cryst. |
| $C_6H_{13}CH(CH)OCOCH-CH-\bigcirc-N-CH-\bigcirc-CH$ $-N-\bigcirc-CH-CHCOOCH(CH_3)C_6H_{13}$ | Iso 133.0°C $S_Q$ 130.5°C $S_O$ 95.0°C Cryst. |

FIG. 9 (Prior Art)

| molecular structure of liquid crystal | phase transferring temperature |
|---|---|
| $C_8H_{17}O\!-\!\bigcirc\!-\!COO\!-\!\bigcirc\!-\!C(=\!O)\!-\!{}^*\!CH(CH_3)\!-\!C_6H_{13}$ | Iso 136° C $S_A$ 108° C $S_C^*$ 49° C $S_{CA}^*$ |
| $C_8H_{17}O\!-\!\bigcirc\!-\!OCO\!-\!\bigcirc\!-\!C(=\!O)\!-\!{}^*\!CH(CH_3)\!-\!C_6H_{13}$ | Iso 132.0° C $S_A$ 100.0° C $S_C^*$ no $S_{CA}^*$ phase |
| $C_8H_{17}COO\!-\!\bigcirc\!-\!\bigcirc\!-\!COO\!-\!{}^*\!CH(CH_3)\!-\!C_6H_{13}$ | Iso 145.2° C $S_A$ 115.0° C $S_C^*$ 103.0° C $S_{CA}^*$ |
| $C_8H_{17}OCO\!-\!\bigcirc\!-\!\bigcirc\!-\!COO\!-\!{}^*\!CH(CH_3)\!-\!C_6H_{13}$ | Iso 101.3° C $S_A$ 92.0° C $S_C^*$ phase |
| $C_{10}H_{21}O\!-\!\bigcirc\!-\!\bigcirc\!-\!COO\!-\!{}^*\!CH(CH_3)\!-\!C_6H_{13}$ | Iso 137.0° C $S_A$ 115.0° C $S_C^*$ 96° C $S_{CA}^*$ |
| $C_9H_{19}O\!-\!\bigcirc\!-\!\bigcirc\!-\!OCO\!-\!{}^*\!CH(CH_3)\!-\!C_6H_{13}$ | Iso 105.0° C $S_A$ 102.0° C $S_C^*$ no $S_{CA}^*$ phase |

FIG. 10 (Prior Art)

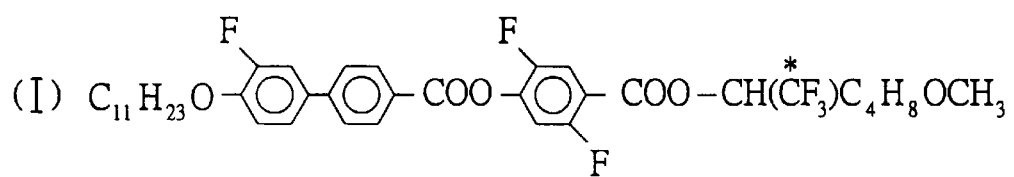
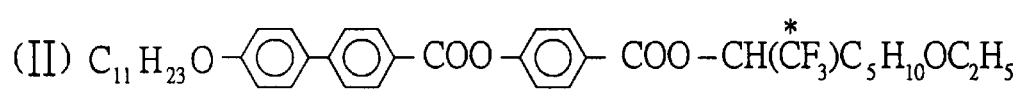
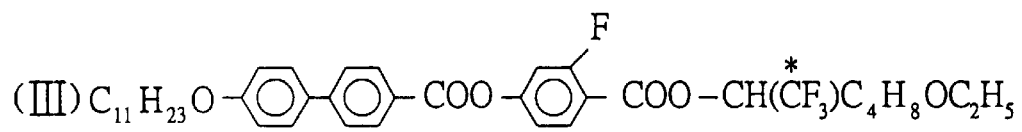
FIG. 11 (Prior Art)

CHIRAL SWALLOW-TAILED LIQUID CRYSTALS AND ITS FABRICATION METHOD

BACKGROUND OF THE INVENTION

1. Field of the Invention

Currently, the antiferroelectric discovered in chiral liquid crystal has a tristable switching property, i.e., in addition to the bistable property of regular ferroelectric liquid crystal, chiral liquid crystal has an antiferroelectric chiral smectic C phrase property, hereinafter called $S_{CA}^*$, or the so-called "third stable state".

Normally, antiferroelectric liquid crystal and ferroelectric liquid crystal have a similar helical structure. The helical structure of antiferroelectric liquid crystal is composed of zigzag bilayers in which, as shown in FIG. 1, the liquid crystal molecules of each two adjacent layers are arranged in reversed directions, therefore the helical structure shows a half helical pitch reflection in a selective reflection spectrum (see (c) and (d) in FIG. 4). In the helical structure of ferroelectric liquid crystal, the liquid crystal molecules of each two adjacent layers are arranged in same direction, as shown in FIG. 3, therefore the helical structure shows a full helical pitch reflection in a selective reflection spectrum (see (a) and (b) in FIG. 4).

The helical structure of antiferroelectric liquid crystal can be surface stabilized to the state like ferroelectric liquid crystal by means of the unwound effect between liquid crystal molecules and interface. Under this surface stabilized state, due to that the liquid crystal molecules are arranged in same direction, ferroelectric liquid crystal shows same direction of molecule dipole as shown in FIG. 5. This feature causes regular ferroelectric liquid crystal to produce pure spontaneous polarization. On the contrary, the liquid crystal molecules of antiferroelectric liquid crystal show a zigzag bilayer structure under the surface stabilized state, as shown in FIG. 6, and the dipole of the molecules is respectively set off, without causing pure spontaneous polarization. This state of reverse molecular arrangement is the third stable state, which can be switched to ferroelectric state by means of the application of an electric field. This switching is the so-called "field induced antiferroelectric to ferroelectric switching". Under the effect of an electric field, the tristable state of antiferroelectric shows particular electric-optical effects, for example, the properties of DC critical electric field and hysteresis. These properties can be used to improve design limitations on LCD viewing angle and contrast ratio.

Further, antiferroelectric liquid crystal further advantages as outlined hereinafter:

(1) The optical axes of the molecules of antiferroelectric liquid crystal molecules are arranged along the alignment, which facilitates to alignment stability;

(2) Under the effect of unwound, antiferroelectric liquid crystal has the third stable state, that effectively eliminates ghost effect and memory effect;

(3) Under the effect of an electric field, antiferroelectric liquid crystal has DC critical electric field and retarding properties, therefore it increases matrix addressing capacity and improves LCD resolution;

(4) Antiferroelectric liquid crystal tends to obtain quasi bookshelf alignment structure, therefore it enables the LCD to have high value of contrast ratio (about 20~30);

(5) Antiferroelectric liquid crystal has rapid response time, which enables current LCD driving technique to be fully utilized, and therefore it is not necessary to develop a new driving technique; and (6) Antiferroelectric liquid crystal has a self-alignment recovery property; therefore it greatly improves LCD's mechanical resisting and heat impact resisting capability.

As indicated above, antiferroelectric liquid crystal plays an important role in the manufacturing and application of photoelectric apparatus. Photoelectric apparatus manufacturers and research units pay much attention to the study of the molecular structure of antiferroelectric liquid crystal materials and the relationship between liquid crystals, so as to design a low-cost, high-performance antiferroelectric liquid crystal material for making LCDs.

2. Description of the Prior Art

The molecular chemical structure of currently developed antiferroelectric liquid crystal materials is similar to ferroelectric liquid crystal molecules. Both are commonly composed of a terminal chiral alkyl chain, a rigid core, a linking group, and a chiral alkyl chain (see FIG. 7). The molecular structure of the terminal chiral alkyl chain, the rigid core and the linking group is the key factor for the formation of antiferroelectric liquid crystal.

The terminal chiral alkyl chain structure in the molecular structure of antiferroelectric liquid crystal has four different kinds as shown in FIG. 8. The polarity of molecular size of the substituent ($R_1$) of the chiral center C* is the main factor that affects the formation of antiferroelectric liquid crystal. Until now, only in the structure molecules of the third kind shown in FIG. 8 is discovered having no antiferroelectric liquid crystal phase, and the structure change of the rigid core has little effect to the formation of antiferroelectric liquid crystal. In materials having different structures of rigid core, as shown in FIG. 9, the change of the rigid core structure from an aromatic ring to an iso-aromatic ring or the one having a substituent does not affect the formation of antiferroelectric liquid crystal. Further, most rigid core is composed of at least three aromatic rings or iso-aromatic rings. Few antiferroelectric. liquid crystal materials have a two-ring structure.

The linking group in an antiferroelectric liquid crystal molecular structure is normally of ester group or ketone group. As illustrated in FIG. 10, the structure, which is linked between the rigid core and the terminal chiral alkyl chain, is most important. In a recent study on the radiation of X-rays and FTIR spectrum to ester materials, it is reported that chiral tail linking ester group, which is linked by —COO—, may produces a bent structure, causing the molecules at two adjacent layers to form a reverse pair arrangement of zigzag bilayer structure. This —COO— linking group increases conjugation of the internal electrons of liquid crystal molecules in molecular long axis, that facilitates the formation of antiferroelectric $S_{CA}^*$ liquid crystal.

Because antiferroelectric liquid crystal has tristable switching property, DC critical electric field property ($E_{th}$) and retarding property, it is appreciated key material for making high quality LCDs. However, due to the constraint of the influence of high $E_{th}$ value and pretransitional effect, conventional antiferroelectric liquid crystal materials do not provide broad viewing angle and high contrast ratio as expected, when used in the fabrication of LCDs.

Till 1996, Japanese scientist Inui mixed the three antiferroelectric liquid crystal materials (I, II and III) indicated in FIG. 11 at different ratio, and made a study to see the result of different mixing ratio on $E_{th}$ value and pretransitional effect. This study shows that changing the mixing ratio of these liquid crystal materials effectively reduces antiferroelectric liquid crystal's $E_{th}$ value, however the change of the mixing ratio causes pretransitional effect more significant. According to Inui's report, when the mixing ratio of I:II:III= 40:40:20, no $E_{th}$ value is found, and its field-induced antiferroelectric to ferroelectric switching shows a V-shaped switching (see FIG. 12). Inui give the name of "Thresholdless antiferroelectric liquid crystals; TLAFLCs" to this antiferroelectric liquid crystal mixture. These thresholdless antiferroelectric liquid crystals have the following properties:

(1) Great tilt angle (>35°);
(2) Low driving voltage (<2V/$\mu m^{-1}$);
(3) Ideal gray scale;
(4) Fast antiferroelectric to ferroelectric switching time (<50µs);
(5) High contrast value (>100); and
(6) Broad viewing angle (>60°).

The aforesaid properties eliminate the gray scale problem occurred during the fabrication of a passive matrix addressing (PM) surface stable ferroelectric liquid crystal display, and also improve the drawback of being difficult to obtain a high contrast ratio commonly existed in regular active matrix (AM) or thin film transistor (TFT) addressing type deformed-helix ferroelectric liquid crystal displays and passive matrix addressing type antiferroelectric liquid crystal displays.

SUMMARY OF THE INVENTION

In view of the numerous advantages of the aforesaid thresholdless antiferroelectric liquid crystals (TLAFLCs), the inventor invented the present invention of novel chiral swallow-tailed liquid crystals, which is synthesized from a chiral material. The chiral material is composed of the compound of alkyl(s)-2-{6-[4-(4'-akyloxyphenyl) benzoyloxy]-2-naphthyl}propionates. The chiral center of this compound is directly linked to its rigid core, and the chiral tail of this compound is linked with a swallow-tailed group. The chiral center and the swallow-tailed group are arranged at the same side in the molecular structure of the compound. These structural characteristics enable the chiral material to have same property of threadholdless antiferroelectricity, and the advantage of simple manufacturing process. The chiral material shows an optimum application effect in liquid crystal displays.

BRIEF DESCRIPTION OF THE DRAWINGS

FIG. 8 is a schematic drawing showing different structures of antiferroelectric liquid crystal molecular terminal chiral alkyl chain FIG. 9 is a schematic drawing showing the effect of a rigid core structure on an antiferroelectric liquid crystal.

FIG. 10 is a schematic drawing showing the effect of a linking group to an antiferroelectric liquid crystal.

FIG. 11 is a schematic drawing showing the molecular structure of three conventional antiferroelectric materials.

DETAILED DESCRIPTION OF THE PREFERRED EMBODIMENT

The present invention provides novel chiral swallow-tailed liquid crystals having thresholdless antiferroelectricity. The novel chiral swallow-tailed liquid crystals are synthesized from a chiral material. The chiral center of the chiral material is directly linked to its rigid core, and its chiral tail is linked with a swallow-tailed group. The common equation of the chiral material is as the chemical formula shown below:

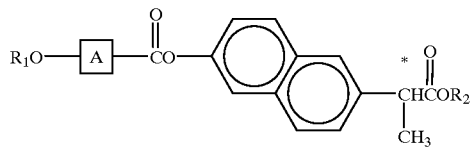

in which $R_1=\!\!-\!\!C_mH_{2m+1}$, $R_2=\!\!-\!\!(CH_2)qCH(C_nH_{2n+1})_2$, m=6–20, q=0,1, n=1,2,3, A represents the rigid core. The rigid core has the following molecular structure:

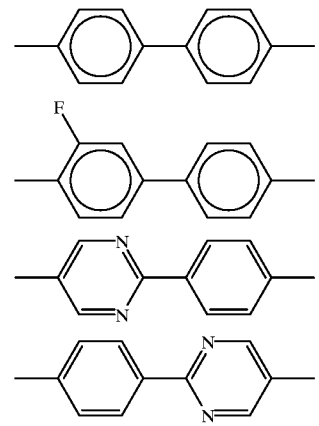

From the above chemical formula, it is apparent that the chiral center and swallow-tailed group of the compound are arranged on the same side. This structural feature enables the compound to have thresholdless antiferroelectricity property. This compound can be prepared by means of the following synthesis.

(1)dissolving 0.025 mol (s)-2-(6-methoxy-2-naphthyl) propionic acid, 0.0275 mol, alkanols having a formula $HO(CH_2)_qCH(C_nH_{2n+1})_2$, wherein q and n are as defined above 0.275 mol dicyolohexylcarbodiimide (DCC) and 0.025 mol 4-dimethylaminopyridine (DMP) in 100 ml dicholoromothane, then stirring up the solution under room temperature for a predetermined length of time (for example, about 5 days), then refining the solution to remove impurities, so as to obtain a first intermediate, namely, alkyl(s)-2-(6-methoxy-2-naphthyl) propionates.

(2) dissolving the first intermediate, namely, alkyl(s)-2-(6-methoxy-2-naphthyl) propionates thus obtained in 60 ml dicholoromothane, then adding 0.025 mol tribromoborane to the solution, then stirring up the solution under −20° C. for a predetermined length of time (for example, about 5 minutes), and then stirring up the solution under 0° C. for a predetermined length of time (for example, about 50 minutes) to let a chemical reaction be occurred, and then refining the solution to remove impurities, and at final applying hexane to the solution, causing the solution to be crystallized into a second intermediate, namely, alkyl(s)-2-(6-hydoxy-2-naphthyl) propionates.

(3) Mixing 0.0116 mol 4-(4'-alkyoxphenyl) benzonic acid, 0.0105 mol alkyl(s)-2-(6-hydoxy-2-naphthyl) propionates, 0.0126 mol dicyolohexylcarbodiimide (DCC), 0.011 mol 4-dimethylaminopyridine (DMP) and 3 ml terahydrofuran, then stirring up the mixture under room temperature for a predetermined length of time (for example, about 5 days, so as to obtain 80–90% yields of chiral materials of the present invention.

The chemical formulas of the aforesaid two intermediates are as follows:

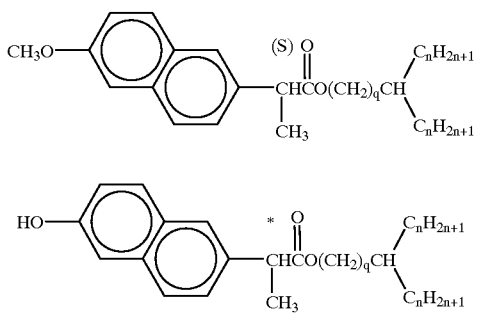

As indicated in the above chemical formulas, the chiral center and the swallow-tailed group are arranged on the same side, and the final produce has the same property.

In order to show the material properties of the compound, following tests are made.

Figure 13:
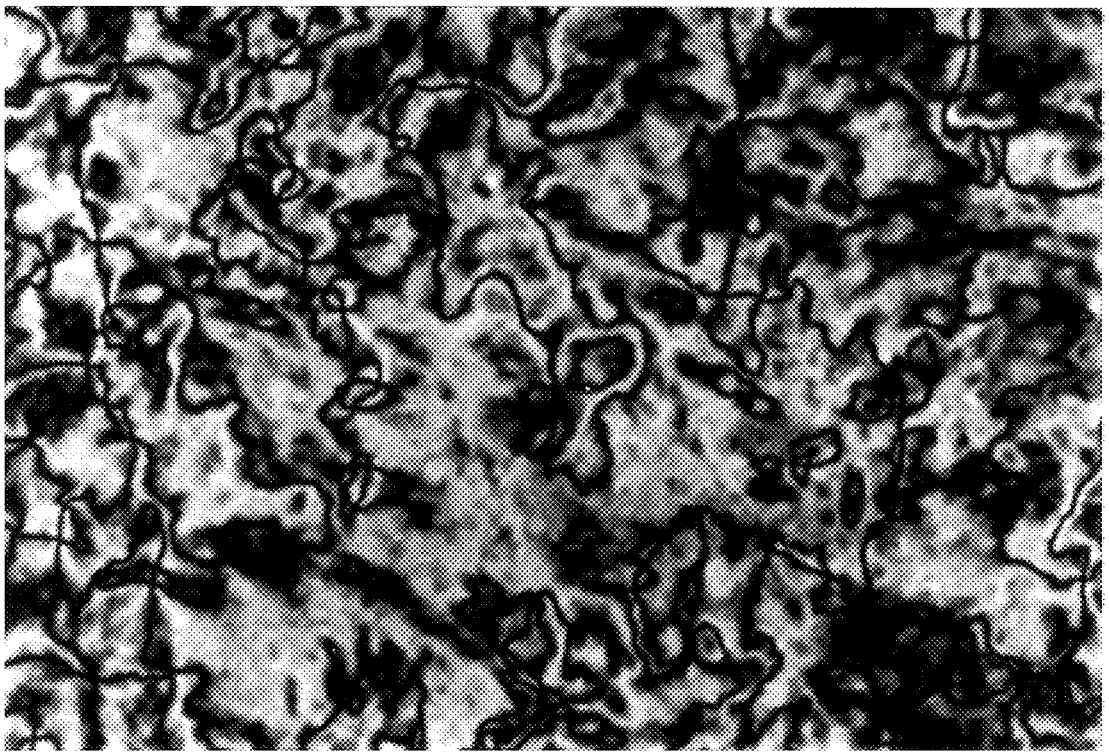
FIG. 13 illustrates the streaks in the material of the present invention obtained through an optical schlieren method

(1) Schlieren test: At first, the finished product of alkyl (s)-2-{6-[4-(4'-alkyloxyphenyl)benzoyloxy]-2-naphthyl}propionates is put on a carrier, then covered with a glass cover plate, and then heated to a liquid status under a polaroid microscope, and a pattern of streaks like FIG. 13 is appeared after the temperature has been dropped to a certain level. From the pattern of streaks, the defect of S=¼ singularity, which is commonly seen in regular ferroelectric liquid crystals is observed, and the defect of S=½, which is commonly seen in regular antiferroelectric liquid crystals, can also be observed. Therefore, the test result indicates the compound having the property of an antiferroelectric liquid crystal.

Figure 1:
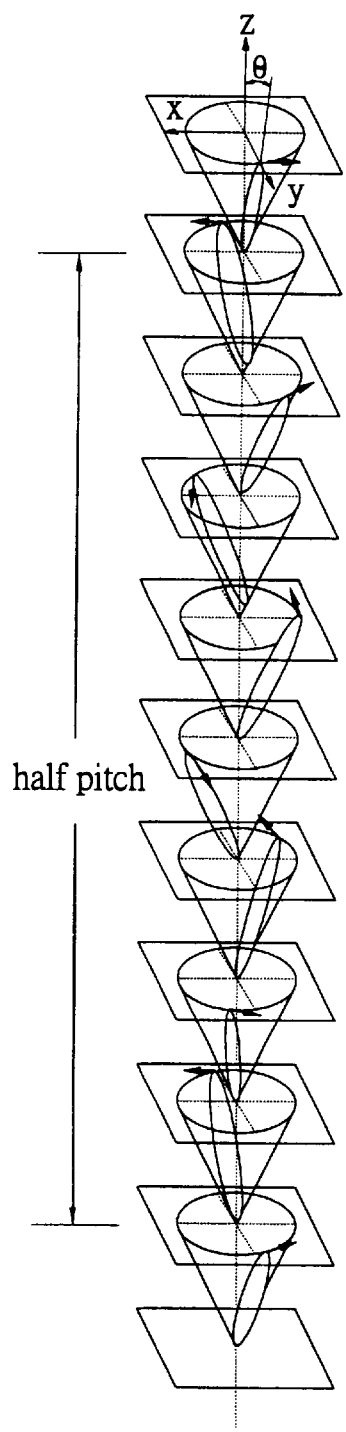
FIG. 1 is a schematic drawing showing the molecular structure of a helical antiferroelectric liquid crystal.
Figure 2:
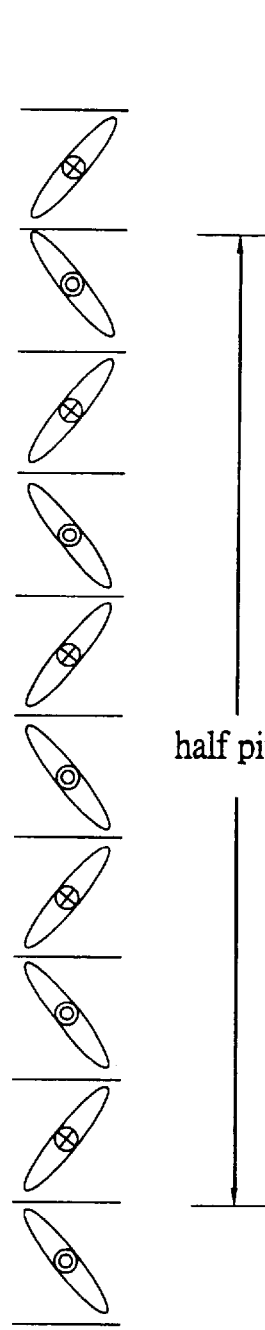
FIG. 2 is a schematic drawing showing the molecular structure of an unwound antiferroelectric liquid crystal.
Figure 3:
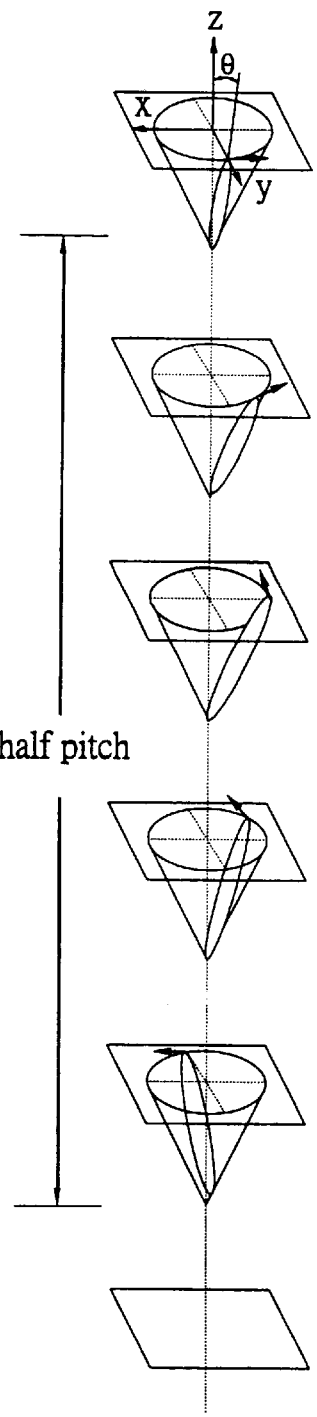
FIG. 3 is a schematic drawing showing the molecular structure of a helical ferroelectric liquid crystal.
Figure 4:
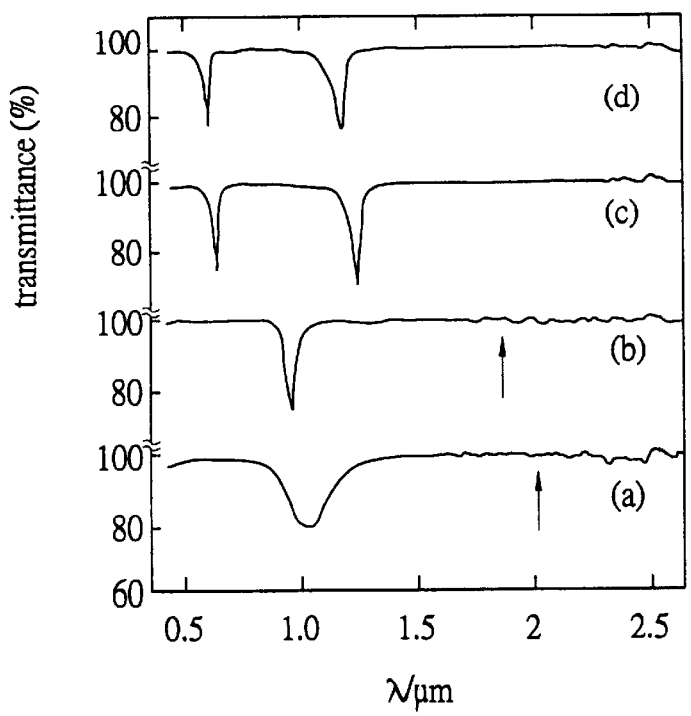
FIG. 4 is a schematic drawing showing the selective reflection spectrum of a ferroelectric liquid crystal and an antiferroelectric liquid crystal.
Figures 5, 6:
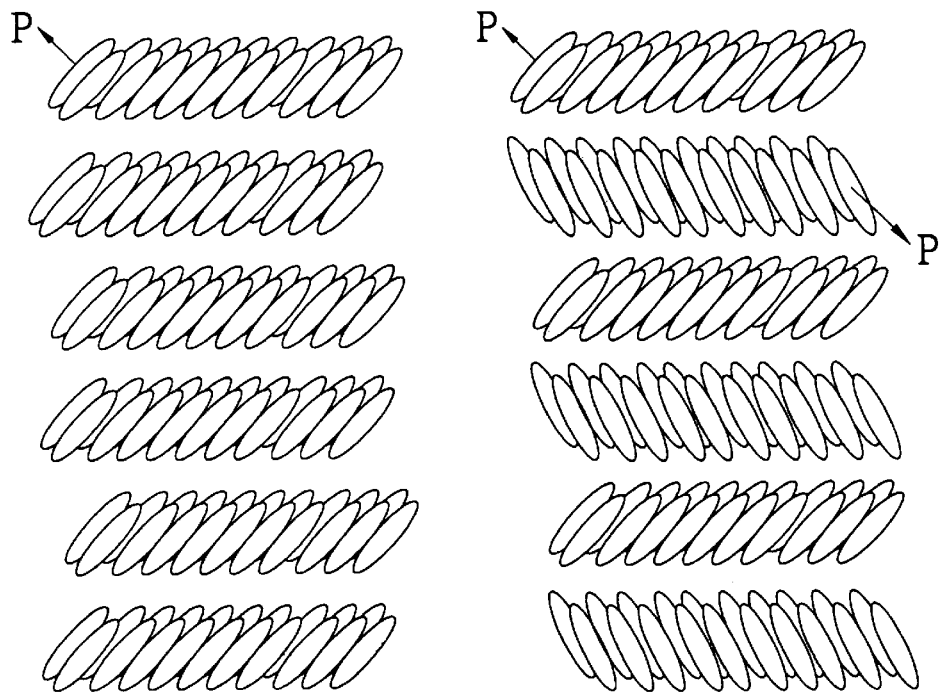
FIG. 5 is a schematic drawing showing the arrangement of unwound molecules of a ferroelectric liquid crystal.
FIG. 6 is a schematic drawing showing the arrangement of unwound molecules of an antiferroelectric liquid crystal.
Figure 7:
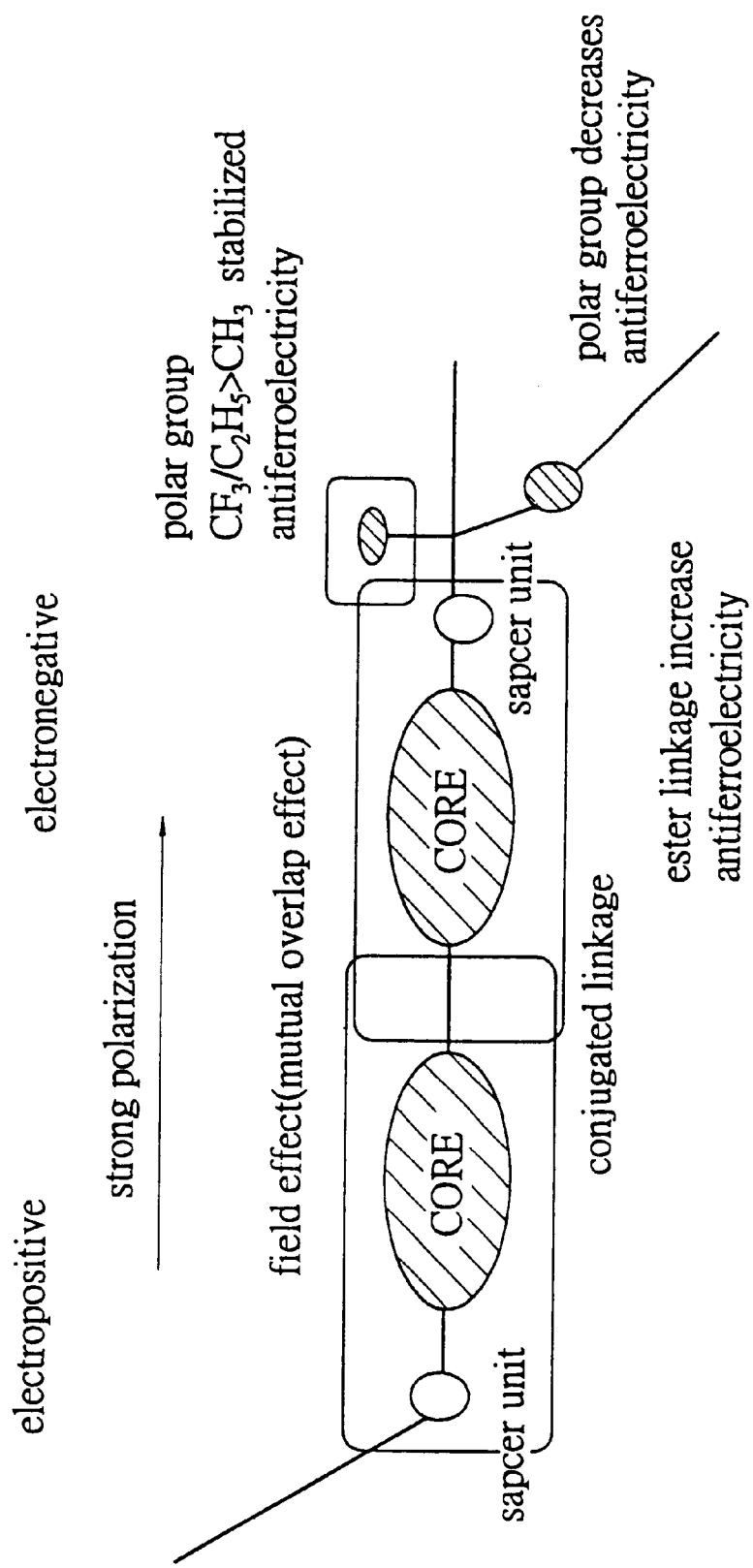
FIG. 7 is a schematic drawing showing the conjugated linkage of the molecules of an antiferroelectric liquid crystal.
Figure 12:
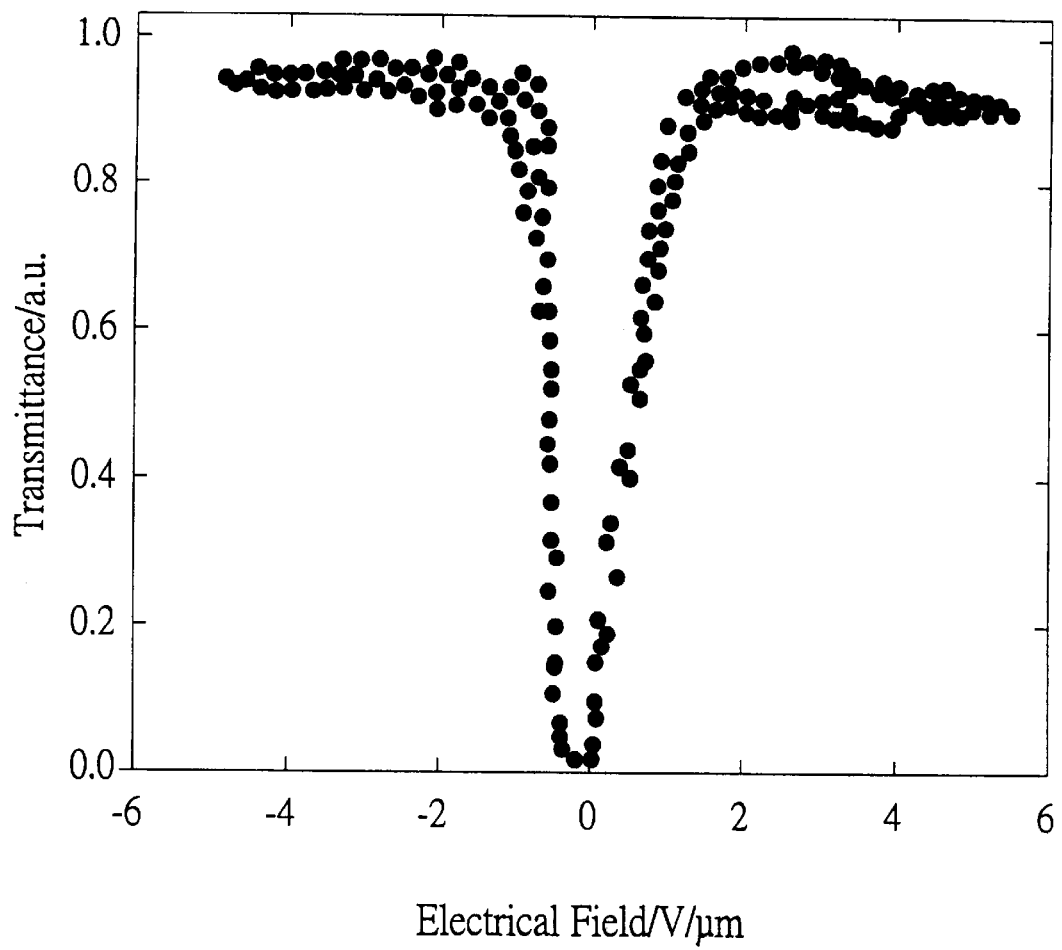
FIG. 12 is a schematic drawing showing the V-shaped switching of the mixture of the three materials shown in FIG. 11.
Figure 14:
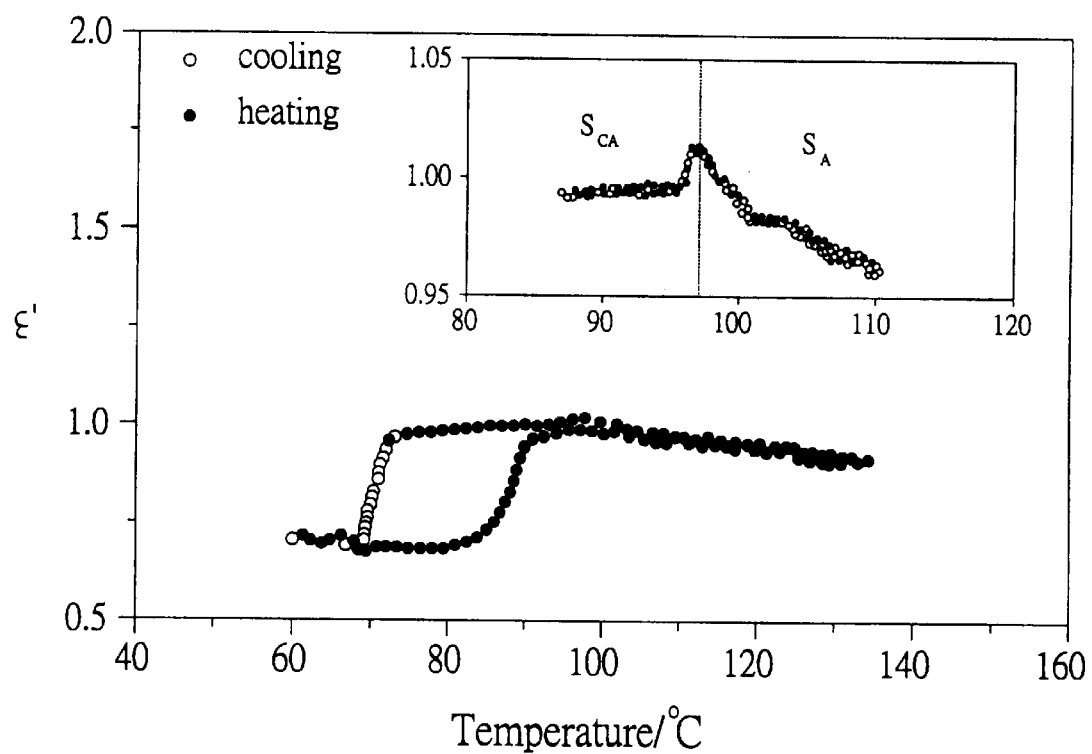
FIG. 14 illustrates the result of a dielectric permittivity test made on the material of the present invention.

(2) Dielectric permittivity test: Normally, in antiferroelectric liquid crystals, each two adjacent layers of the molecules, unlike the arrangement of the molecules in ferroelectric liquid crystals, are arranged in reversed directions, see FIGS. 5 and 6, and this property causes the dipole of the molecules in antiferroelectric liquid crystals to set off respectively. Therefore, unlike the high dielectric permittivity value of ferroelectric liquid crystals, the dielectric permittivity value of antiferroelectric liquid crystals is low. When using photoelectric measuring means to measure alkyl(s)-2-{6-[4-(4'-alkyloxyphenyl)benzoyloxy]-2-naphthyl}propionates, the dielectric permittivity value shown in very low (see FIG. 14). Therefore, it is apparent that the compound of the present invention has same low dielectric permittivity property of antiferrorelectric liquid crystals.

Figure 15:
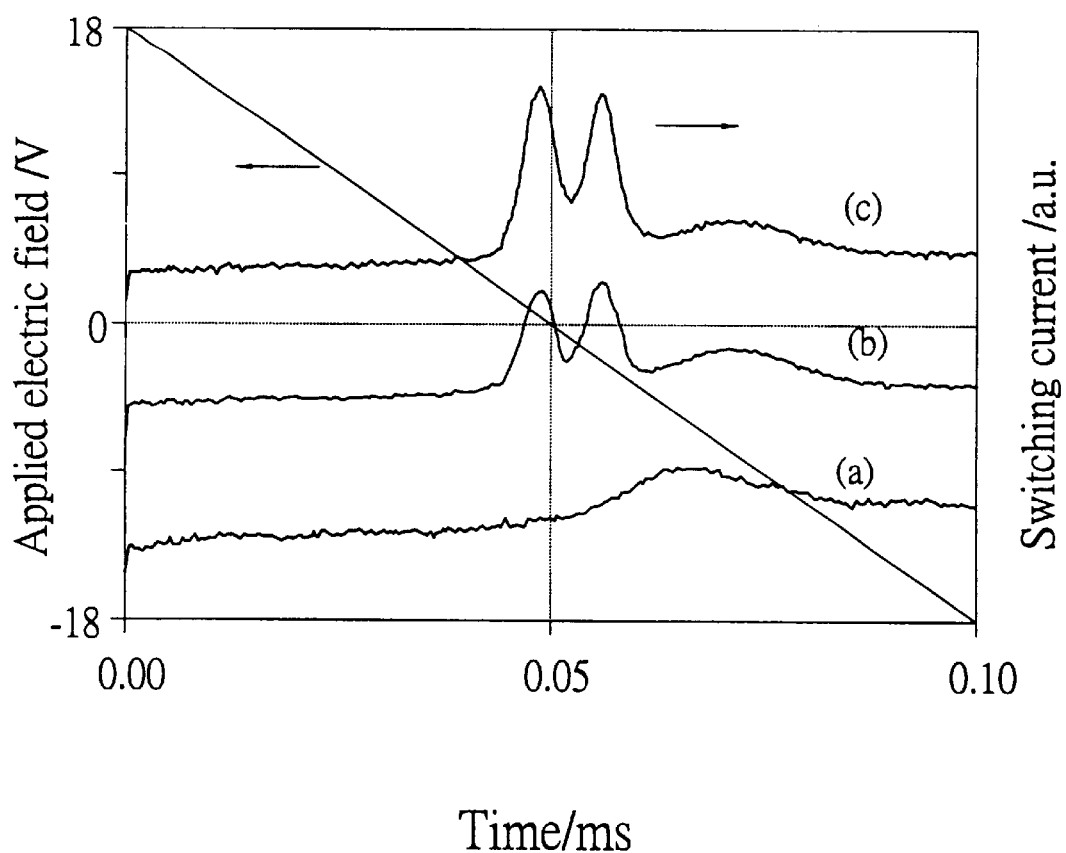
FIG. 15 illustrates the result of a switching behavior test made on the material of the present invention.

(3) Switching behavior test: After a photoelectric test on alkyl(s)-2-{6-[4-(4'-alkyloxyphenyl)benzoyloxy]-2-naphthyl}propionates, the result is shown in FIG. 15. As indicated, two switching current peaks are produced during switching current, and the property of antiferroelectric liquid crystals of field induced antiferrorelectric to ferroelectric is shown during surface stabilized state.

Figure 16:
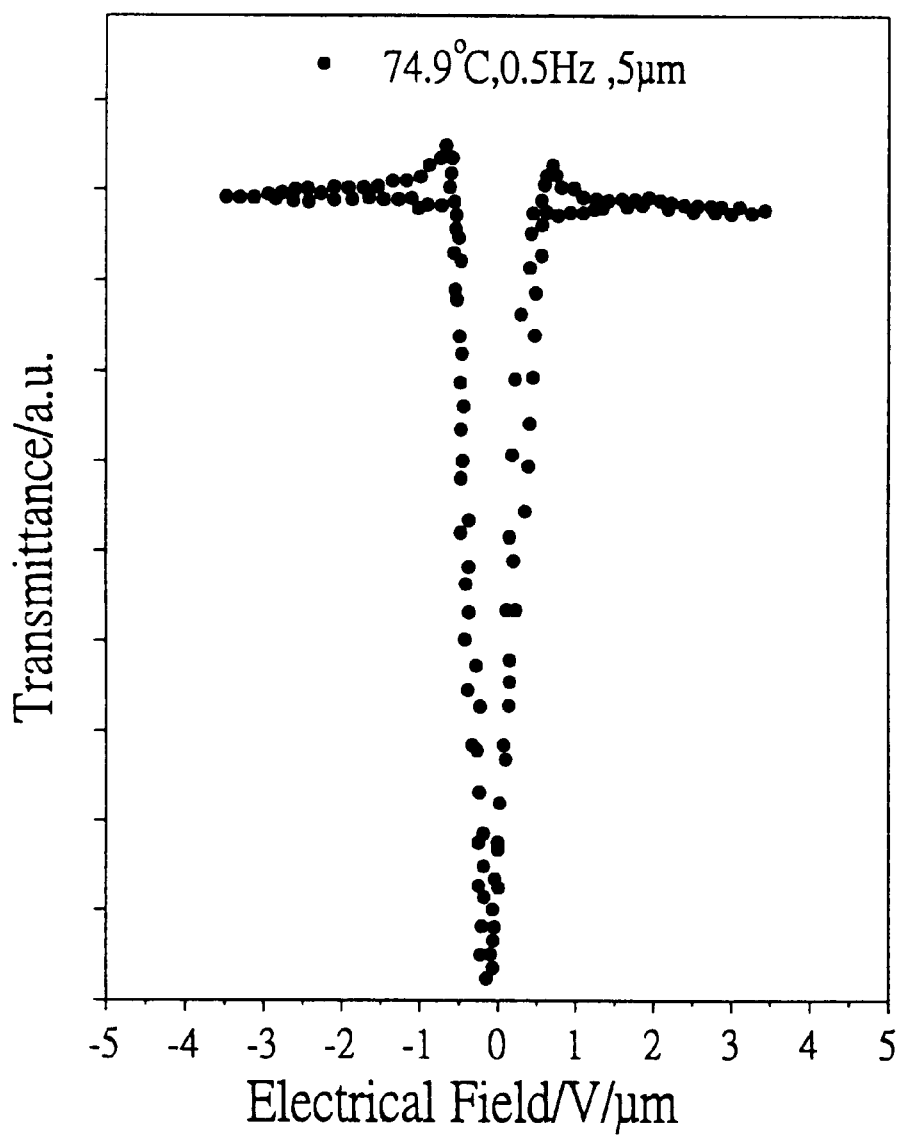
FIG. 16 illustrates the result of a V-shaped switching test made on the material of the present invention.

(4) V-shaped switching: As shown in FIG. 16, when electric current passes through the compound of the present invention, the switching of field induced antiferroelectric to ferroelectric is a V-shaped switching, therefore the material of the present invention has thresholdless antiferroelectricity property.

As indicated above, the compound of the present invention is a kind of antiferroelectric liquid crystal material having thresholdless antiferroelectricity property. Its manufacturing process is simple. Therefore, it is important in liquid crystal mixing techniques. When used in the production of liquid crystl displays, the compound of the present invention shows a satisfactory effect.

While only one embodiment of the present invention has been shown and described, it will be understood that various modifications and changes could be made thereunto without departing from the spirit and scope of the invention disclosed.

What the invention claimed is:

1. A chiral swallow-tailed liquid crystals synthesized from chiral material comprised of alkyl(s)-2-{6-[4-(4'-alkyloxyphenyl)benzoyloxy]-2naphthyl}propionates having a rigid core, a chiral center directly linked to the rigid core, a chiral tail, and a swallow-tailed group linked to the chiral tail, and having a formula

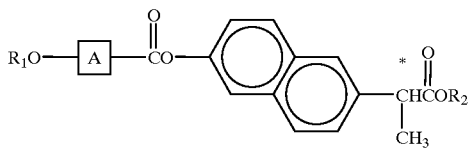

in which $R_1 = -C_mH_{2m+1}$, $R_2 = -(CH_2)_qCH(C_nH_{2n+1})_2$, m=6–20, q=0, 1 and n=1,2 or 3, A represents a rigid core, having a formula

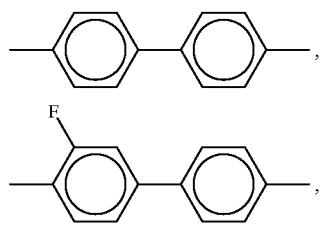

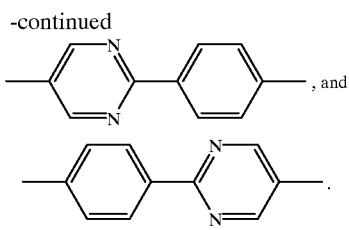, and

2. The chiral swallow-tailed liquid crystals of claim 1 wherein in the common equation q is equal to 1.

3. The chiral swallow-tailed liquid crystals of claim 1 wherein in the common equation n is equal to 2.

4. The chiral swallow-tailed liquid crystals of claim 1 wherein in the common equation n is equal to 3.

5. The chiral swallow-tailed liquid crystals of claim 1 wherein the molecular structure of said rigid core A is as follows:

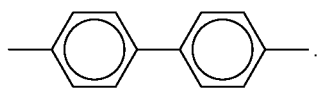

6. The chiral swallow-tailed liquid crystals of claim 1 wherein the molecular structure of said rigid core A is as follows:

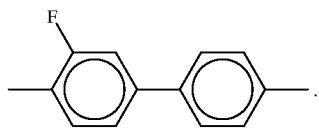

7. The chiral swallow-tailed liquid crystals of claim 1 wherein the molecular structure of said rigid core A is as follows:

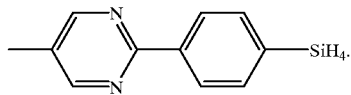

8. The chiral swallow-tailed liquid crystals of claim 1 wherein the molecular structure of said rigid core A is as follows:

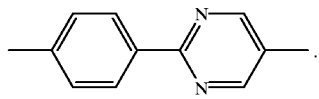

9. A method for fabricating chiral swallow-tailed liquid crystals comprising the steps of:

(i) dissolving 0.025 mol (s)-2-(6-methoxy-2-naphthyl) propionic acid, 0.0275 mol alkanols having a formula $HO(CH_2)_qCH(C_nH_{2n+1})_2$, 0.276 mol dicyolohexylcarbodiimide (DCC) and 0.025 mol 4-dimethylaminopyridine (DMP) in 100 ml dicholoromethane, then stirring up the solution under room temperature for a predetermined length of time, then refining the solution to remove impurities, so as to obtain a first intermediate alkyl(s)-2-(6-methoxy-2-napthyl) propionates;

(ii) dissolving said first intermediate alkyl(s)-2-(6-methoxy-2-naphthyl) propionates thus obtained in 60 ml dicholoromothane, then adding 0.025 mol tribromoborane to the solution, then stirring up the solution under −20° C. for about 5 minutes, and then stirring up the solution under 0° C. a predetermined length of time to let chemical reaction be occurred, and then refining the solution to remove impurities, and at final applying hexane to the solution, causing the solution to be crystallized into a second intermediate alkyl(s)-2-(6-hydroxy-2-naphthyl) propionates;

(iii) mixing 0.0116 mol 4-(4'alkyoxyphenyl) benzoic acid, 0.0105 mol alkyl(s)-2-(6-hydroxy-2-naphthyl) propionates, 0.0126 mol dicyolohexylcarbodiimide (DCC), 0.011 mol 4-dimethylaminopyridine (DMP) and 3 ml terahydrofuran, then stirring up the mixture under room temperature for a predetermined length of time, so as to obtain a an 80–90% yield of chiral material; q=0, 1 and n=1,2 or 3.

10. The chiral swallow-tailed liquid crystals fabrication method of claim 9, wherein the solution in step (i) is stirred up under room temperature for about 5 days.

11. The chiral swallow-tailed liquid crystals fabrication method of claim 9, wherein the solution in step (ii) is stirred under 0° C. for about 50 minites.

12. The chiral swallow-tailed liquid crystals fabrication method of claim 9, wherein the mixture in step (iii) is mixed under room temperature for about 5 days.

13. The chiral swallow-tailed liquid crystals fabrication method of claim 9, wherein the first intermediate obtained from step (i) has the follow chemical equation (1)

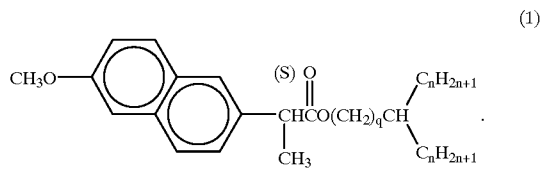

14. The chiral swallow-tailed liquid crystals fabrication method of claim 9, wherein the second intermediate obtained from step (ii) has the following chemical equation:

(2)

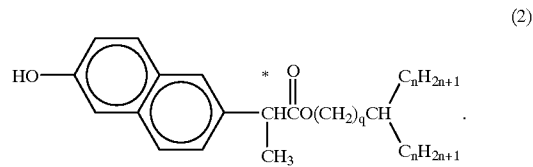

* * * * *